United States Patent

[19]

Hydro

[11] 4,032,531
[45] June 28, 1977

[54] PIPERIDINE DERIVATIVES

[75] Inventor: William R. Hydro, Bel Air, Md.

[73] Assignee: The United States of America as represented by the Secretary of the Army, Washington, D.C.

[22] Filed: Dec. 3, 1969

[21] Appl. No.: 882,757

[52] U.S. Cl. .......................... 260/293.64; 424/267
[51] Int. Cl.² ........................................ C07D 211/06
[58] Field of Search .............. 260/294.3 A, 293.64; 424/267, 275, 285

[56] References Cited

UNITED STATES PATENTS 3,408,356  10/1968  Horovitz ..................... 260/294.3 A Primary Examiner—Leland A. Sebastian
Attorney, Agent, or Firm—Nathan Edelberg; Robert W. Church

[57] ABSTRACT

The method and compositions of matter useful as incapacitating agents having the formula

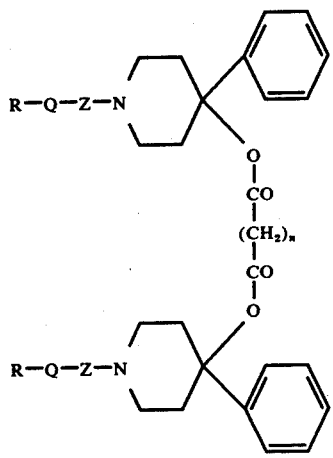

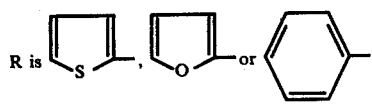

Z is a hydrocarbon chain of 1 to 4 carbon atoms;
$n$ is a whole number from 1 to 8.

7 Claims, No Drawings

PIPERIDINE DERIVATIVES

DEDICATORY CLAUSE

The invention described herein may be manufactured, used, and licensed by or for the Government for governmental purposes without the payment to me of any royalty thereon.

This invention is directed to new polymeric N-substituted piperidine compounds and their method of preparation.

It is an object of this invention to provide compositions of matter which produce decrease in muscle tone in the subject.

It is a further object of this invention to incapacitate subjects with the compounds of this invention.

The previous methods for minimizing the undesirable side-effects have been by modifying the structure with the insertion of a moiety or by co-administering with other compounds or combinations thereof have proven, in general, to be ineffective in accomplishing the desired results.

The unexpected results flowing from my investigation was that in preparing the polymeric compound instead of observing a more intensive observation of reaction signs of greater muscle tone by increasing the molecular weight the exact opposite effects resulted in a decrease in muscle tone.

Piperidines are known with aryl and lower acyloxy substituents in the 4-position carbon atom of the piperidine ring. Lower alkyl and aralkyl groups are attached to the nitrogen atom of the piperidine ring.

Various N-substituted-4-phenyl-4-substituted piperidines illustrated below can be used as the starting monomer in accordance with this invention. Carabateas et al, J. Med. Pharm. Chem. Vol 5, p. 913 (1962) published the compounds (3-hydroxy-3-phenylpropyl)-4-phenyl-4-piperidinol and (3-oxo-3-phenylpropyl)-4-phenyl-4-piperidinol. Elpern et al, J. Am. Chem. Soc., 80, 4916 (1958) disclose various 4-acyloxy-1-aralkyl-4-phenyl-piperidines. The compounds 1-[2-(2-thenoyl)ethyl]-4-phenyl-4-piperidinol and 1-[2-(2-furoyl)ethyl]-4-phenyl-4-piperidinol employed as the starting monomers and their method of preparation are disclosed in my copending application Ser. No. 687,392, filing date Dec. 1, 1967, now U.S. Pat. No. 3,919,243.

An investigation was instituted to prepare compounds which are more effective incapacitating agents than have been previously known. As a result of my investigation, the N-substituted-4-phenyl-4-substituted piperidine compounds, discussed above, gave rise, in accordance with this invention, to non-linear polymeric compounds having the following structure:

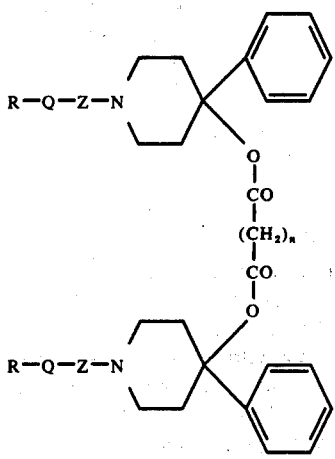

-continued

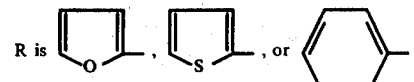

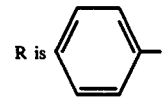

Z is a hydrocarbon chain of 1 to 4 carbon atoms and $n$ is a whole number from 1 to 8;

When Q is $-CH=$,   Z is $(=)CH-CH_2-$,

Q is $-OCH_2-$,   Z is $-CH_2-CH_2-$

R is $n$ is defined as above.

At room temperature a solution comprising from 1–6 moles of a dicarboxylic acid halide containing from $C_3$ to $C_{10}$ carbon atoms in a solvent is added to a mixture containing 1 mole of N-substituted-4-phenyl-4-substituted piperidines, an excess of neutralizing agent, forming a reacted mixture which is filtered. The filtrate is evaporated forming a syrup which is dissolved in diethyl ether, then dried and filtered. The ether filtrate is cooled and stirred with anhydrous hydrogen chloride until precipitation of the corresponding chloride which is the desired inventive polymeric compound.

The pharmacological evaluation of the diester piperidinium compounds of this invention for potency was determined by the administering intravenously various proportions (mg/kg) of the compounds upon mice using the method of "The Search For And Selection Of Toxic Chemical Agents for Weapons Systems" disclosed in the Edgewood Arsenal, Md. publication (CRDL SOP 70-3, 6 May 1965). $LD_{50}$ is the lowest dose in mg of compound per kilogram of animal to be lethal in 50% of the tested animals. $MED_{50}$ is the lowest dose in mg per kilogram of animal required to give any visible physiological effect (i.e. mydriasis, muscle reflex) in 50% of the tested animals.

The compounds may be utilized in any munition suitable for handling relatively non-toxic agents such as spray tanks, shells, bombs, rockets and aerosol generators which have been previously devised for chemical warfare agents.

EXAMPLE 1 a. A solution at room temperature comprising 1.22 g of adipyl chloride in 20 ml of chloroform is added dropwise over about a 14 minute time period to a mixture containing 9.4 g sodium carbonate, an excess, 1.6 g water, 3.5 g 1-[2-(2-thenoyl) ethyl]-4-phenyl-4-piperidinol, and 200 ml chloroform forming a reaction mixture then agitating for about 5 hours, filtering the reaction mixture and then removing the volatiles by evaporating in vacuo on a rotating film evaporator leaving a residue as a syrup. The residue is dissolved in sodium-dried diethyl ether, dried over anhydrous magnesium sulfate for about 30 minutes, and then filtered. The filtrate, ether solution, is cooled to about 0° C and to the stirring filtrate anhydrous hydrogen chloride is added until precipitation of the corresponding chloride is complete which is about 8 minutes. The precipitate is removed, washed with ether and dried over phosphorus pentoxide overnight in a vacuum desiccator giving rise to a crude white product. The crude polymer product, about 4.3 g, was recrystallized from ethyl alcohol yielding polymeric white crystals, m.p. 181° – 182° C. The structure of bis {1-[2-(2-thenoyl)ethyl]-4-phenyl-4-piperidino} adipate dihydrochloride monohydrate was confirmed by infrared analysis.

Anal. calcd for $C_{42}H_{50}Cl_2N_2O_6S_2 \cdot H_2O$: C, 60.64; H, 6.30; Cl, 8.52; N, 3.37; $H_2O$ 2.2. Found: C, 61.1; H, 6.4; Cl, 8.9; N, 3.6; $H_2O$ 2.4.

$LD_{50}$ (mice) was 18.0 g/kg
$MED_{50}$ (mice) was 1.8 g/kg

The polymeric compound when tested gave reaction signs of relaxation of the skeletal muscles, that is, a decrease in muscle tone of the trunk and limbs. The related monomer disclosed in my copending case, 1-[2-(2-thenoyl)ethyl]-4-phenyl-4-propionoxy-piperidinum chloride exhibited an increase in muscle tone of the trunk and limbs.

b. The procedure in accordance with (a), supra, was followed with the exception of substituting malonyl chloride for the corresponding adipyl chloride producing the corresponding bis {1-[2-(2-thenoyl)ethyl]-4-phenyl-4-piperidino} malonate dihydrochloride monohydrate.

c. The procedure in accordance with (a), supra, was followed with the exception of substituting sebacoyl chloride for the corresponding adipyl chloride producing the corresponding bis {1-[2-(2-thenoyl)ethyl]-4-phenyl-4-piperidino} sebacate dihydrochloride monohydrate.

d. The procedure in accordance with Example 1 (a), (b) and (c), supra, was followed with the exception of substituting 1-[2-(2-furoyl)ethyl]-4-phenyl-4-piperidinol for the corresponding 1-[2-(2-thenoyl)ethyl]-4-phenyl-4piperidinol producing bis{1-[2-(2furoyl)ethyl]-4-phenyl-piperidino } adipate dihydrochloride monohydrate, bis {1-[2-(2-furoyl)ethyl]-4-phenyl-4-piperidino} malonate dihydrochloride monohydrate, or bis {1-[2-(2-furoyl)ethyl]-4-phenyl-4-piperidino} sebacate dihydrochloride monohydrate.

EXAMPLE 2 a. The procedure in Example 1 (a) was repeated with the exceptions of substituting 1-(3-oxo-3-phenyl)propyl-4-phenyl-4-piperidinol for the corresponding piperidinol and succinyl chloride for the adipyl chloride producing bis [1-(3-oxo-3-phenyl)propyl-4-phenyl-4-piperidino]succinate dihydrochloride, m.p. 171.5° – 173° C, having the following structure:

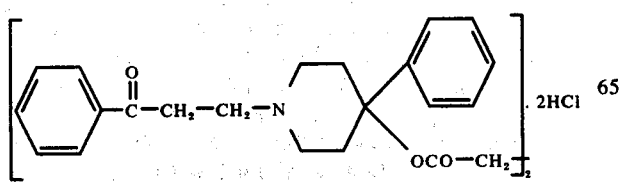

Anal calcd for $C_{44}H_{48}N_2O_6 \cdot 2HCl$: C, 68.30; H, 6.51; Cl, 9.16; N, 3.62; O, 12.41. Found: C, 68.2; H, 6.3; Cl, 9.0; N, 3.9; O, 12.9.

$LD_{50}$ (Mice) = 18.0 g/kg
$MED_{50}$ (Mice) = 5.6 g/kg

The reaction signs are decreased locomotion, rearing, preening and slow respiration.

b. The procedure in (a), supra, was repeated with the exception of substituting glutaryl chloride or sebacoyl chloride for the succinyl chloride giving rise to the corresponding bis [1-(3-oxo-3-phenyl)propyl-4-phenyl-4-piperidino]glutarate dihyrochloride or bis [1-(3-oxo-3-phenyl)propyl-4-piperidino] sebacate dihydrochloride.

EXAMPLE 3 a. The procedure in Example 1 (a), (b) and (c) was repeated with the exception of substituting 1[2-propenyl-3-phenyl]-4-phenyl-4-piperidinol or 1-[3-phenoxypropyl]-4-phenyl-4-piperidinol for 1-[2-(2-thenoyl)ethyl]-4-phenyl-4-piperidinol and producing the polymeric compounds bis {1-(2-propenyl)-3-phenyl-4-phenyl-4-piperidino} adipate dihydrochloride monohydrate; bis {1-(2-propenyl-3-phenyl-4-phenyl-4-piperidino} malonate dihydrochloride monohydrate; bis {1(2-propenyl)-3-phenyl-4-piperidino} sebacate dihydrochloride monohydrate; bis {1-[3-phenoxypropyl]-4-phenyl-4-piperidino} adipate dihydrochloride monohydrate; bis {1-[3-phenoxypropyl]-4-phenyl-4-piperidino} malonate dihydrochloride monohydrate or; bis {1-[3-phenoxypropyl]-4-phenyl-4-piperidino} sebacate dihydrochloride monohydrate.

I claim:

1. A method for producing incapacitating agents the steps including at ambient temperatures reacting a solution containing a dicarboxylic acid halide having from $C_3$ to $C_{10}$ carbon atoms with a mixture containing a N-substituted-4-aryl-4-substituted piperidine of the formula:

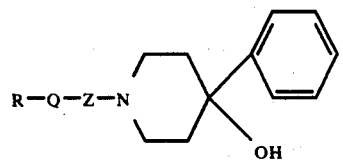

Wherein

R is 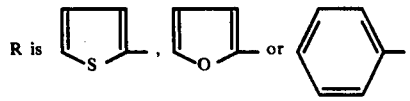

Q is 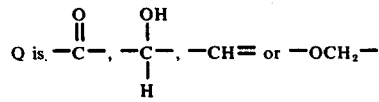

Z is a hydrocarbon chain of 1 to 4 carbon atoms forming a reacted mixture, separating said reacted mixture, dissolving the residuum in a solvent, drying and filtering, cooling the filtrate and treating said filtrate with anhydrous hydrogen halide forming an insoluble non-linear polymeric compound.

2. The method according to claim 1, wherein the solution comprises the acid halide and chloroform.

3. The method according to claim 1, wherein the mixture comprises the substituted piperidine and an excess of neutralizing agent.

4. Compounds of the following formula

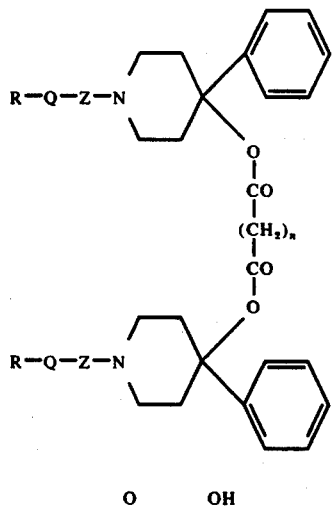

Z is alkylene group of 1 to 4 carbon atoms
n is a whole number from 1 to 4;

When Q is —CH=,    Z is (=) CH—CH$_2$—,

Q is —OCH$_2$—,   Z is —CH$_2$—CH$_2$—

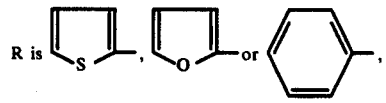

n is a whole number from 1 to 4.

5. The compounds in accordance with claim 4, wherein

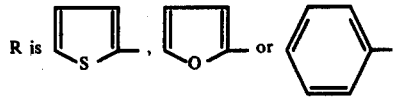

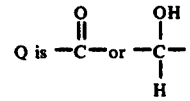

6. The compounds in accordance with claim 4, Wherein
Q is — CH =
Z is = CH— CH$_2$ —
R is

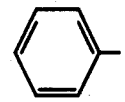

7. The compounds in accordance with claim 4, Wherein
Q is — OCH$_2$ —
Z is — CH$_2$ — CH$_2$ —
R is

* * * * *